United States Patent [19]

Langberg

[11] Patent Number: 5,199,437
[45] Date of Patent: Apr. 6, 1993

[54] ULTRASONIC IMAGER

[75] Inventor: Edwin Langberg, Mt. Laurel, N.J.

[73] Assignee: Sensor Electronics, Inc., Mt. Laurel, N.J.

[21] Appl. No.: 756,510

[22] Filed: Sep. 9, 1991

[51] Int. Cl.$^5$ ............................................. A61B 8/12
[52] U.S. Cl. ............................ 128/662.06; 128/661.01
[58] Field of Search ......... 128/661.01, 662.05–662.06, 128/916

[56] References Cited

U.S. PATENT DOCUMENTS

| | | | |
|---|---|---|---|
| 4,821,731 | 4/1989 | Martinelli et al. | 128/662.06 |
| 4,880,011 | 11/1989 | Imade et al. | 128/662.06 |
| 4,930,515 | 6/1990 | Terwilliger | 128/662.06 |
| 4,951,677 | 8/1990 | Crowley et al. | 128/662.06 |
| 4,985,856 | 1/1991 | Kaufman et al. | 364/522 |
| 5,000,185 | 3/1991 | Yock | 128/662.06 |
| 5,036,855 | 8/1991 | Fry et al. | 128/662.06 X |
| 5,049,130 | 9/1991 | Powell | 128/662.06 X |
| 5,081,993 | 1/1992 | Kitney et al. | 128/662.06 X |
| 5,107,844 | 4/1992 | Kami et al. | 128/662.06 |
| 5,125,410 | 6/1992 | Misono et al. | 128/662.06 |
| 5,131,397 | 7/1992 | Crowley | 128/662.06 |

OTHER PUBLICATIONS

Brinkley, J. F. et al, "UTS 3D Imaging & Volume from Arbitrary Sector Scans", UTS in Med. & Biol., vol. 4, No. 4 (1978) pp. 317–327.

Bom, N. et al, "An Ultrasonic Intracardiac Scanner", Ultrasonics, Mar. 1972.

Schwarz, H. P. et al, "A 100-Element UTS Circular Array for Endoscopic Application in Medicine and NDT", Annual Conf. IEEE EMB, vol. 12, No. 1, pp. 287–290 (1990).

Goldwasser, S. M. et al, "Physician's Workstation with Real-Time Performance", IEEE CG&A, Dec. 1985, pp. 44–57.

Meyer, C. R. et al, "Feasibility & Dx Value of Catheter-Based UTS Intravascular Imaging", 1988 UTS Symp. pp. 805–808, 1988.

Primary Examiner—Francis Jaworski

[57] ABSTRACT

The invention provides an intracavitary ultrasonic scanner with a helical scan. Mechanical and electronic steerable array implementations of the helical scan are described. A plastic cover sheath, filled with coupling fluid, covers the probe of the scanner. Portions of probe are porous allowing the coupling fluid to penetrate to the outside of the sheath. An improved polar coordinate decoding system provides an accurate control of the scan and allows storage of scan information in voxel memory.

4 Claims, 3 Drawing Sheets

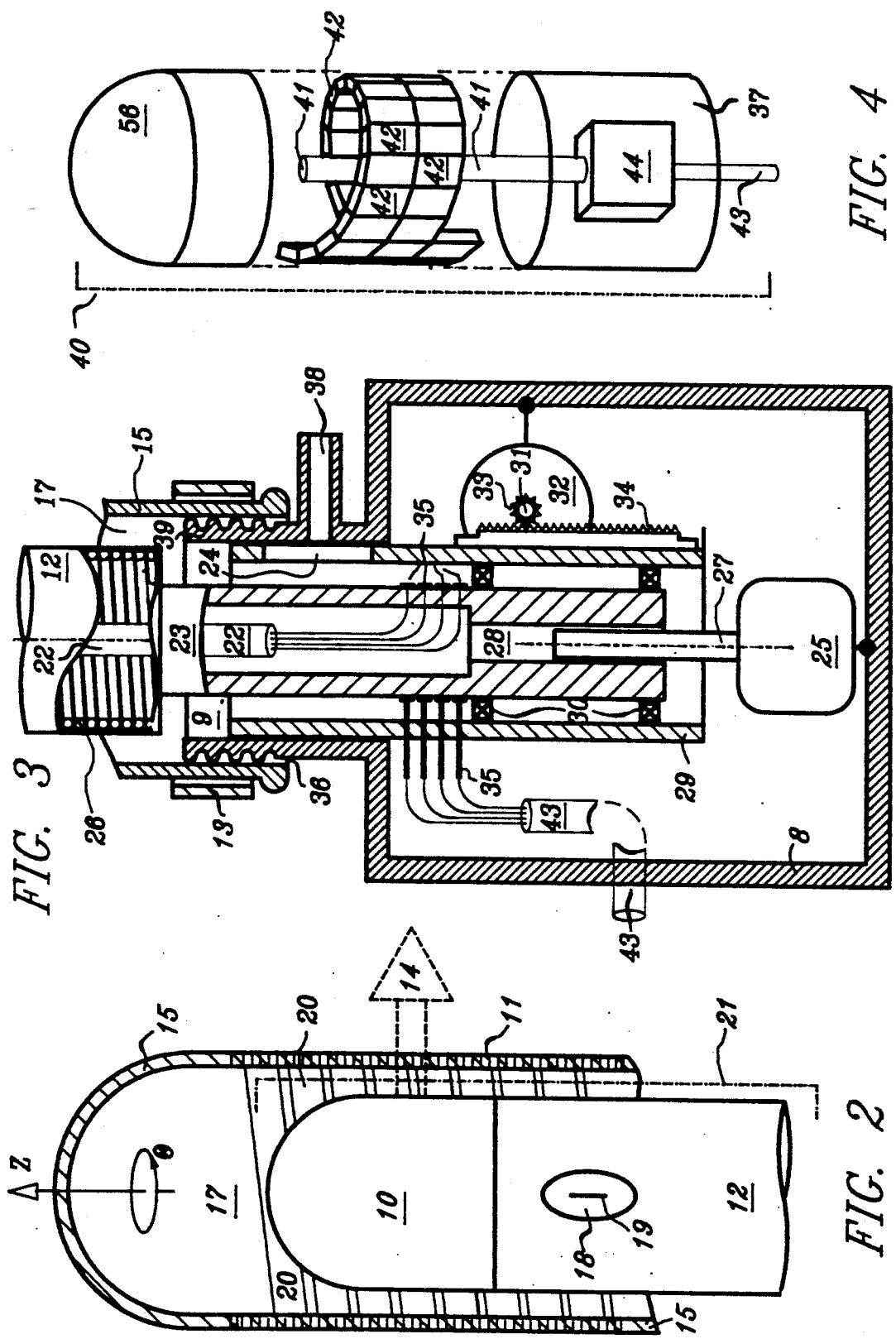

ULTRASONIC IMAGER

FIELD OF INVENTION

The present invention relates to ultrasonic imaging systems such as used for imaging features of internal parts of a human body, and a method for performing an intracavitary scan using an imaging system.

BACKGROUND OF THE INVENTION

Ultrasonic scanning systems which use pulse-echo ultrasound to provide information regarding the position, configuration, composition, and other internal features of human body organs are widely used in medicine. There are some anatomical situations in which improved ultrasonic images can be obtained by scanning from within the bodily cavities and vessels. Intracavitary ultrasonic scanners have been extensively described in the literature, e.g., in U.S. Pat. No. 4,869,258 of W. Hetz. Common types of intracavitary scanners are available for insertion into a rectum, vagina, and alimentary tract. Intracavitary scanners permit close contact with the region of interest, allowing higher ultrasonic frequencies to be used thus providing better resolution than extracorporeal scanners. Intracavitary scanners can also avoid problems with overlying structures, especially bone and those containing gas. A device technologically related to intracavitary scanner is an intravascular ultrasonic scanner such as described in U.S. Pat. No. 5,000,185 of P. G. Yock used for examination of blood vessels.

Both intracavitary and intravascular scanners comprise a probe-like shaft used to place a scanning transducer, located at a tip of the shaft, at the desired location inside the bodily cavity or vessel. Both scanner categories are therefore often referred to as probe scanners, such nomenclature having been used, e.g., in U.S. Pat. No. 4,972,839 of B. A. Angelsen and in U.S. Pat. No. 4,930,515 of R. A. Terwilliger.

To aid in the following description, it is convenient to define a cylindrical coordinate system where the z axis coincides with the axis of the shaft at its tip, r is the radial direction from the shaft axis, and $\Theta$ is the rotational angle measured around the shaft axis. A voxel (volume element) in such a cylindrical coordinate system is identified by a parallelepiped of the size $dr_i$, $r_i \cdot d\Theta_j$, and $dz_k$, centered at the $r_i$, $\Theta_j$, and $z_k$ coordinates. The scanned volume can then be divided into closely fitting voxels, each identified by its coordinate values of $r_i$, $\Theta_j$, and $z_k$.

Many display modes are being used in probe scanners. The closest art to the present invention is a plan position indicator (PPI) mode: It is an r,$\Theta$ polar coordinate display where the radial distance r corresponds to radial ultrasound beam echo delay time, the rotational angle $\Theta$ corresponds to the beam rotation around the axis of the shaft, and intensity corresponds to a processed amplitude of an echo signal at each position of r and $\Theta$. The PPI mode limitation to an r,$\Theta$ display plane represents a serious shortcoming. For example, a rectal scan of a prostate then produces only a single cross-sectional plane of the organ, which limits its diagnostic value. By manual insertion or retraction of the shaft, one can obtain the r,$\Theta$ display in planes corresponding to different values of z along the axis of the shaft, yet each presentation remains in an r,$\Theta$ plane.

There are several requirements for accurate registration in the three-dimensional cylindrical coordinate system r,$\Theta$,z needed to establish an accurate correspondence between anatomical features and their scanned voxel value as stored in the computer memory voxel space: one requirement is that the transducer and the shaft be moved along a straight z axis identifiable with respect to the cavity; another requirement is that the transducer orientation be such that the beam direction is truly radial. Yet another requirement is that the axial (z) coordinate and the rotational ($\Theta$) coordinate of the beam be accurately determined.

Current PPI-type probe scanner devices have no means to control the z-axis motion within the cavity. Further, in current scanner practice, measurement of the shaft position coordinates is typically made at the proximal base of the shaft. The shaft design is therefore a compromise: the shaft needs to be flexible enough to follow the possibly convoluted path required to reach the desired location in the bodily cavity, yet rigid enough to minimize the error in coordinates between the decoders at the proximal shaft base and the transducer at the distal shaft tip. When the shaft is relatively short, straight, and rigid, this technique works well. However using this method, it is difficult to design scanners for distant organs e.g., for the uterus where the shaft has to be long and flexible; in such cases, due to the dynamics of torque transmission, there is a variable delay in the rotational angle between the proximal and distal ends of the shaft, leading to an error in the measured value of the $\Theta$ scan coordinate. In order to bypass the error between the proximal angle measurement and the distal value of the $\Theta$ coordinate, U.S. Pat. No. 4,880,011 of S. Imade et al uses a decoder located at the distal catheter end. Imade's decoder adds significant bulk to the scanner.

An alternative to a mechanical rotation is an electronically steerable circular array of sensors, which by electronic switching and phase shifting accomplishes beam rotation. Such arrays for ultrasonic probe application, working in a circular PPI mode, have been described in the literature (e.g., see "A 100-Element Ultrasonic Circular Array For Endoscopic Application in Medicine and NDT" by H. P. Schwarz et al in the Annual International Conference of the IEEE Engineering and Biology Society, Vol. 12, No. 1:287-290, 1990). A steerable circular array still requires mechanical motion in the z direction.

In state-of-the-art ultrasonic probe scanners, voxel space storage and processing is not used, largely due to registration errors; the display of the probe scan is in real time, i.e., the information displayed is obtained from the scanner data with only minimal processing delay. A shortcoming of such presentation is that the repetitive stream of scan data is irretrievably two-dimensional, and cannot be used to improve the resolution or to reduce "speckle". "Speckle" is a random scintillation pattern on the display, an artifact unrelated to the anatomical structure, resulting from an interference between the waves backscattered from within the coherent ultrasonic resolution cell.

OBJECT AND SUMMARY OF THE INVENTION

A primary object of the present invention is to provide a new and useful ultrasonic imager especially suited for use in body cavities, e.g. the uterus, and to a new and useful method of employing same.

It is also a principal object of the present invention to provide an improved ultrasonic probe-scanning system to overcome or substantially reduce the above-noted problems arising in previously known systems.

In accordance with the invention aspect, there is provided in such an imager, a coordinated axial and rotational scanning beam motion, such as a helical scan, by means of which voxels adjacent to the probe-scanning system are explored systematically in three dimensions and signal values accurately representative of reflections from each voxel are derived.

In another aspect, the present invention comprises a plastic cover sheath, lubricated by acoustic coupling fluid, which maintains sonic transparency and alignment with bodily cavity walls, provides a stable rotational bearing for the shaft, and contains fiduciary coordinate marks for coordinate decoding.

In still another aspect, the present invention comprises the storage and processing of ultrasonic echo data, such that each memory address is associated with a corresponding voxel in the r,Θ,z coordinate system via an algorithm driven by the helical scan. On multiple scans, the echo amplitude stored at a memory address is averaged with previous values, thus reducing speckle and improving resolution.

Still another aspect of the present invention involves a method of scanner guidance, placement, and operation as described hereinafter.

Other objects and features of the invention will become more apparent from the following detailed description, taken in connection with the accompanying drawings, wherein:

BRIEF DESCRIPTION OF THE DRAWINGS

FIG. 2 is a schematic longitudinal sectional view of the distal end of the probe of FIG. 1;

FIG. 3 is a schematic longitudinal sectional view of the proximal end of the probe of FIG. 1;

FIG. 4 is a schematic perspective view of a preferred embodiment of an electronically-scanned imager probe in accordance with the invention in another form.

DETAILED DESCRIPTION OF THE INVENTION

Figure 1:
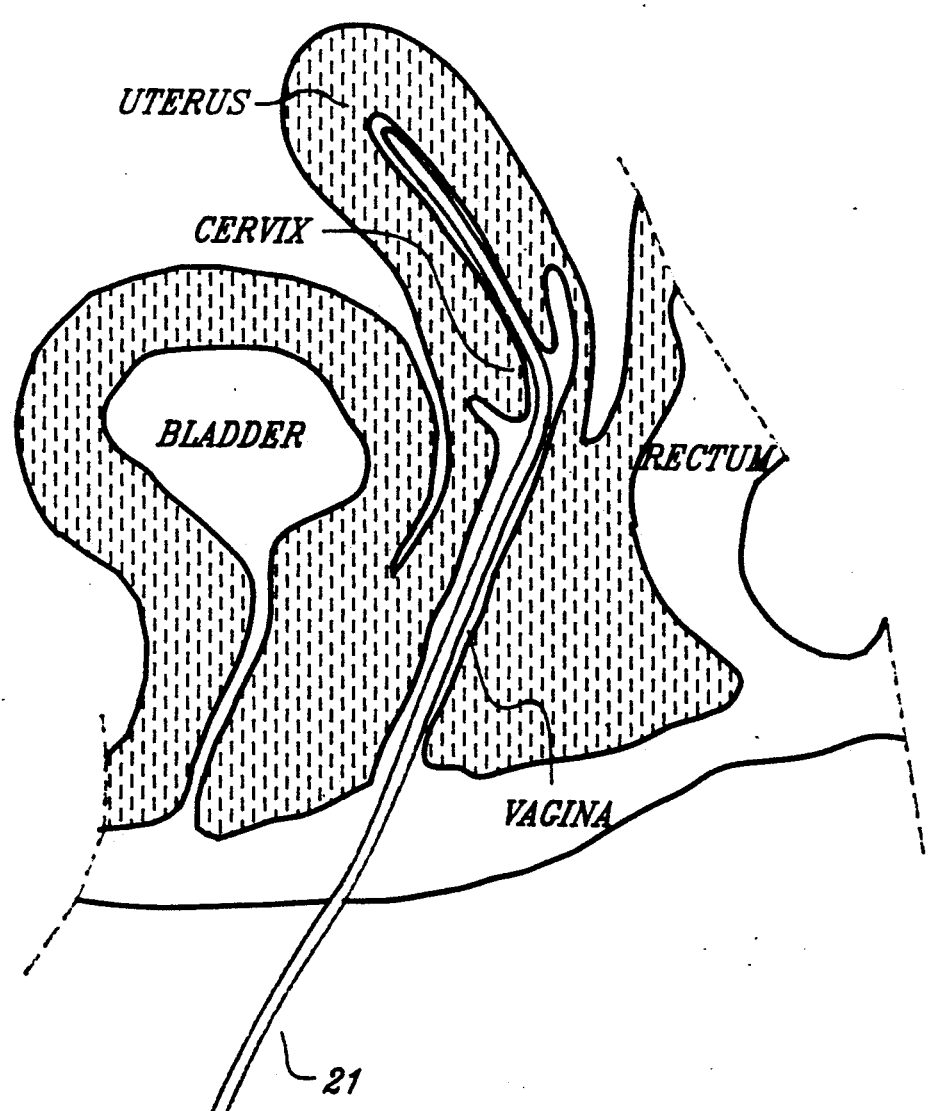
FIG. 1 is a longitudinal elevational view, partly in section, of a mechanically-scanned imager probe in accordance with a preferred embodiment of the invention in place in a bodily cavity.

Considering first especially the over-all arrangement of the invention shown in FIG. 1, an imager probe assembly 6 comprises an imager probe 21 positioned centrally within a flexible plastic sheath 15 (both shown in FIG. 2), which in turn extends into a uterus to perform ultrasonic exploration of the uterus by a scanning ultrasonic transducer 10 mounted at the distal end of the probe. As will be described later herein in FIG. 3, the probe is secured at its distal end to a stationary coupling 39 and is filled with an acoustic coupling fluid 17 under pressure, supplied through inlet port 38. The probe 21 is secured to the distal end of base 23 which in turn is supported on spin bearings 30 to a translator 29, so as to be both axially and rotationally movable with respect to a stationary housing 8 and thus also with respect to the uterus. A stepping motor 32 controls the axial position of the probe 21 with respect to the uterus, and a stepping motor 25 controls the rotational angle of the probe. A flexible electrical cable 43 provides connection to associated monitoring and control equipment described hereinafter.

More particularly in the example, the transducer 10 is made of lead zirconate titanate (PZT) piezoceramic material and otherwise follows a well-known design for formation of an ultrasonic radial (r-direction) scanning beam 14 (e.g., see "Ultrasound transducers for pulse-echo medical imaging" by J. W. Hunt, M. Arditi, and F. S. Foster in *IEEE Transactions on Biomedical Engineering*, Vol. BME-30, No. 8: 453–481, 1983, and "Feasibility and Diagnostic Value of Catheter-Based Ultrasonic Systems for Intravascular Imaging: In Vitro Comparisons with MRI" by C. R. Meyer, E. H. Chiang, D. W. Fitting, D. M. Williams, and A. J. Buda in 1988 *Ultrasonics Symposium*: 805–808, 1988).

Probe 21, Comprising an entire helically-moving assembly, is covered by the sheath 15, shown in a hatched cross section in FIG. 2. The sheath is made of thin, flexible plastic material such as latex. A space between probe 21 and sheath 15 is filled with acoustical coupling fluid 17. Coupling fluid 17 is applied at a slightly positive pressure through inlet port 38 (shown in FIGS. 1 and 3). Coupling fluid 17 provides good acoustical transmission and has acoustical impedance comparable with tissue, resulting in reduced reflection by improved interface matching. The coupling fluid 17 can be as simple as saline solution, although the coupling fluid often includes gelling agents (e.g., see Acoustic Characteristics of PVA Gel by K. Hayakawa in 1989 *Ultrasonics Symposium*, 1989). The stationary sheath 15 when placed in a bodily cavity provides a bearing and axial alignment for helical scanning motion of probe 21. The coupling fluid 17 serves, in addition to its acoustical role, as a lubricant for such bearing for helical motion for the shaft inside of the sheath.

A portion 11 of sheath 15, extending axially for a full distance of a helical scan, comparable to the length of the uterus, is made from a porous plastic material so that the acoustical coupling fluid 17 penetrates through the porous material of the top portion 11 of sheath 15 into a space between the sheath and wall of a scanned bodily cavity thereby displacing any air bubbles; assuring a good acoustical coupling between the transducer 10 and scanned tissue; and helping to align sheath 15 with an axis of the scanned bodily cavity.

A magnetic readout head 18 with a magnetic gap 19 extending along a z direction is placed at an outer radius of probe 21. Magnetic head 18 senses the magnetization of a thin and flexible magnetic coating 20 embedded on the inside diameter of the sheath 15 in a helical pattern. Digital code, recorded in the coating 20 and read by the magnetic head 18, provides a coordinate code signal used to calibrate incremental steps in Θ and z coordinates of the scanning beam 14. Since the readout of the coordinate code is made near the distal end of the probe, any twist in the flexible shaft 12 has no effect on accuracy of coordinate readout, thereby providing the coordinate accuracy required for proper voxel memory processing. The shaft 12 can therefore be made quite long and flexible if needed for reaching a distant bodily cavity.

Alternatively, if the coupling fluid is transparent to optical radiation, the coordinate decoding can be implemented optically with an optical readout head where 19 is a beam of optical radiation, and 18 is a detector or radiation reflected from an optically encoded pattern 20.

A proximal end of the preferred embodiment of the mechanically-scanned imager probe is shown in FIG. 3. Because of disparity of sizes, the scale of individual elements is adjusted for clarity. Flexible shaft 12, shown partially in a cross section at the top of FIG. 3, is made of a helical steel wire coil 26, in the form of a so called Bowden cable capable of transmitting motion, even when flexed. An electrical cable 22 is substantially co-axial with the flexible shaft 12, and cable 22 moves together with shaft 12 as the cable carries electrical signals to and from the transducer 10 and from the magnetic head 18 to slip rings 35.

A mechanical drive causes transmission of a helical motion to the base 23 driving the flexible shaft 12. A helical motion coupler comprises a means for generation of the helical motion of shaft 12 from a rotation of the two stationary stepping motors 25 and 32. Helical motion is carried from the base 23 to the flexible shaft 12 and through shaft 12 to transducer 10, causing a helical scan of the ultrasonic beam 14. Rotation (in the Θ direction) of shaft 12 is imparted by a key-shaped shaft 27 of Θ-stepping motor 25. An axial opening 28 in base 23 matches the key-shaped shaft 27 thus coupling the rotation without translational constraint. Base 23 is mounted on bearings 30 to the translator 29 and is supported by a neck 9 in housing 8. Translation of shaft 12 (in the z direction) is imparted through a pinion gear 33 on a shaft 31 of the z-stepping motor 32. Pinion gear 33 engages a rack 34 mounted on translator 29. The translator 29 is constrained from rotation by guides (not shown) which are parallel to the z axis. Rotation is thereby combined with translation to cause helical motion of base 23.

Helical motion could be obtained from a single-motor mechanical drive. The advantage of the two-motor design is that the ratio of the pulse repetition rates of motors 25 and 32 is used to control the pitch angle of the helical scan. The slip rings 35 maintain an electrical connection between the moving cable 22 and stationary input/output (I/O) cable 43. Flex at the beginning of cable 43 takes up translating motion of the slip rings 35, fastened to the translator 29.

A proximal end opening 36 of sheath 15 slips unto a corrugated coupling 39, and is held by a ring clamp 13. The interior of the sheath 15 is internally connected to inlet port 38 through neck 9 of housing 8, interior of translator 29 and through opening 24 in the wall of translator 29.

An alternative implementation of the imager probe is shown in FIG. 4, showing a view of three segments of probe 40. A top segment comprises tip 56 of probe 40. A middle segment comprises a helically-stepped array of transducers 42. A radial ultrasonic beam is generated and helically scanned by electronic steering of a partially shown 128-element array of transducers 42. The advantage of this implementation, as compared with the mechanical implementation, is that once inserted, no mechanical motion of the probe is required. The disadvantage is the required number of transducers and more complex electronics.

Individual transducers 42 are connected through cable 41 to a steering integrated circuit (IC) chip 44 embedded in a flexible shaft 37 of probe 40, shown in the bottom segment FIG. 4. Since a switching and multiplexing function is carried out in the IC chip 44, the leads 41 from individual transducers 42 to chip 44 are much shorter than full length of the probe 40 traversed by the I/O cable 43. The helical transducer array geometry and the location of the IC chip close to the array in the catheter is novel and leads to new results, such as a three dimensional scanning capability. The methodology of the implementation of the steering circuit 44 will be obvious from the teaching of prior art of switching and phase shift operations by extrapolation, from circular to helical scan steering. Steering of a circular array is described e.g., by N. Bom, C. T. Lancee, and F. C. Van Egmond in *Ultrasonics*, March: 72–76, 1972.

Figure 5:
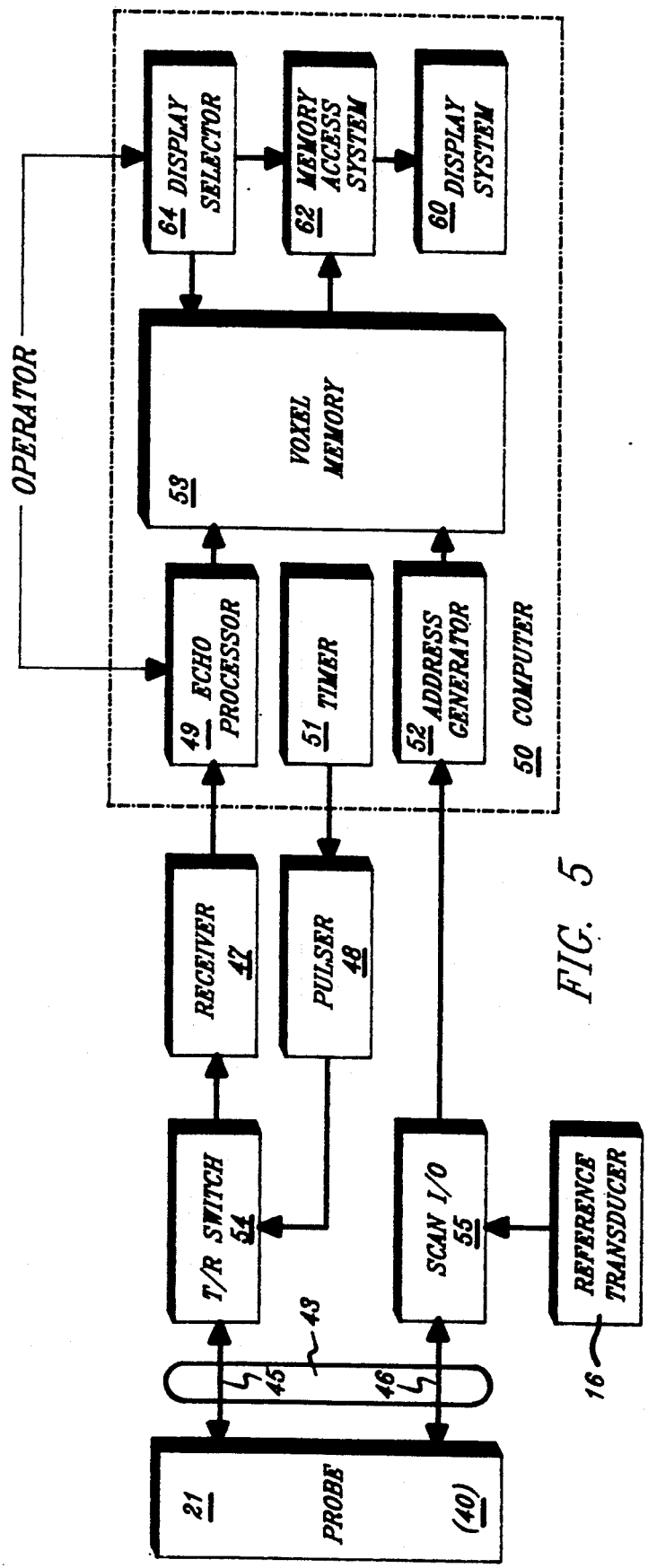
FIG. 5 is a block diagram of a preferred electrical system for operating the probe in accordance with the invention in one of its aspects.

A block diagram of a control and processing system is shown in FIG. 5. This block diagram is applicable to both mechanically-scanned and electronically-scanned imager probe implementations. Probe 21 or 40, depending on the probe type, is connected through the I/O cable 43, carrying pulse/echo lines 45 and synch/scan lines 46 to a transmit/receive (T/R) switch 54 and a scan I/O circuit 55, respectively. An analog echo signal is amplified and digitized in a receiver 47 and subsequently processed in an echo processor 49. A transmit pulse is generated in a pulser circuit 48 in response to a signal originated in a timer 51. Echo processor 49 and timer 51 are parts of a computer. 50. Only functional components particular to the imager probe are indicated within the computer 50 block.

The scan I/O circuit 55 receives decoded coordinate information and drives the electronic or mechanical helical scan. An address generator circuit 52 converts coordinate information into a voxel memory address so that a scan of a voxel in anatomical space corresponds repetitively to the same address in voxel memory 53.

This one-to-one correspondence between an anatomical three-dimensional space and the voxel memory address allows averaging and other statistical and geometrical operations involving stored and the current echo signal content. In addition to processing the current echo signal, the echo processor 49, on the operator command can optionally also compare the current echo signal with the signal stored in voxel memory 53 and update the stored value, based on a selected algorithm.

Conversion of scan data stored in the voxel-based cylindrical coordinate object space into a two-dimensional display of a cross section of arbitrary orientation, e.g., a display of an r,z plane at a specified Θ, gives the system three-dimensional capability comparable with a tomographic display manipulation at a fraction of the cost. Storing of information and recomputing of various display views from the voxel space is a well established art (e.g., see U.S. Pat. No. 4,985,856 by Kaufman and Bakalash). The bulk of this art is however directed at x-ray and MRI (magnetic resonance imager) rather than ultrasonic displays, and with application to Cartesian rather than cylindrical coordinates. In such systems, unlike the system described here, reprojection of display views to other than a r,Θ slice orientation in real-time (in <30 ms) requires powerful computers with customized architecture (e.g., see "Physician's Workstation with Real-Time Performance", by Samuel M. Goldwasser et al in *IEEE Computer Graphics and Applications*, Vol. 5, No. 12:44–57, 1985).

The block diagram depicted in FIG. 5 to the left of voxel memory 53 represents the scanner data acquisition. The three blocks on the right of the voxel memory 53 represent the readout of the accumulated data. Display selector 64 is controlled by an operator to select the arbitrary three dimensional plane to be displayed on the display system 60. Display system 60 typically comprises a cathode-ray tube, but can also provide hard copy printouts. Display selector 64 controls the transformation of the voxel memory data to the buffer memory in the memory access system 62, to be used to control the beam intensity and position of the cathode ray tube of the display system 60, and thereby to form the selected type of display in the desired anatomical plane. Unlike a PPI type of scan limited to the r - Θ plane, an r - z plane, or a plane inclined with respect to the z axis can be depicted to optimize diagnostic information.

A method of application of the imager probe is discussed in conjunction with the scan of the uterus because the uterus is difficult to scan using the state of the art intracavitary ultrasonic scanners, and an improvement is medically significant and desirable. The first step is to place the sheath 15, prefilled with coupling fluid 17, onto a steerable guide wire. The steerable guide wire is not a part of the apparatus described in previous figures but it is frequently used in medical practice. Using the steerable guide wire, the sheath is inserted, possibly with fluoroscopic guidance, into the uterus. As shown in FIG. 1, the tip of the sheath is positioned at the distal end of the uterus thus providing an absolute anatomical calibration reference for the z-coordinate. After the sheath is positioned, the steerable guide wire is withdrawn and the scanner probe is inserted through the sheath, and the sheath is attached to the housing.

The absolute anatomical reference for the Θ-coordinate is in this example provided by a reference transducer 16, shown in a block form in FIG. 5. Transducer 16 is an ultrasonic microphone with a directional pattern concentrated along a plane. In a uterine scan, the reference transducer 16 is placed on the abdomen above the uterus with the directional pattern coinciding with a sagittal plane of the body. (The spine and the tip of the nose of the patient define the sagittal plane of the body). As the ultrasonic beam rotates in the Θ direction, the amplitude of the ultrasonic signal intercepted by reference transducer 16 reaches a peak when the beam is in the sagittal plane, thus providing an absolute anatomical reference for the Θ coordinate.

There has therefore been provided an ultrasonic imager which derives and stores three-dimensional voxel information with respect to body material adjacent the ultrasonic transducer, by scanning the ultrasonic beam axially and rotationally, either mechanically or electrically. The location of each voxel is identified by a set of values of radius r, rotational angle Θ and axial position z, and corresponding positions are provided in a memory device in which values corresponding to reflections from each voxel are stored. The stored voxel information can then be accessed and displayed in any of a variety of formats and displays. While the scanning is preferably helical along the axis, this specific type of scan is not essential so long as the voxel location r,Θ,z is known for each reflected bit of ultrasonic energy; for example, the pitch of the helix can be varied during the scan depending on the desired resolution in different regions of the uterus or, the scan could be in the form of circles about the axis, with a small axial jump between successive circular scans. To implement the system, a probe and sheath arrangement is provided wherein the surrounding sheath provides guidance and a bearing for the rotating probe, the interior of the sheath being supplied with acoustic fluid under pressure to rigidify the sheath and to flood the space between sheath and body tissue with the acoustic fluid during operation; the sheath also provides support for coded reference elements which identify the Θ and z of the scanning beams at any time.

While the invention has been described with particular references to specific embodiments in the interest of complete definiteness, it will be understood that it may be embodied in a variety of forms diverse from those specifically shown and described, without departing from the spirit and scope of the invention.

What is claimed is:

1. An improved ultrasonic intracavitary imaging system of a type in which ultrasonic transducer means located on a probe is connected to a control and processing system, the transducer means generating a scanning ultrasonically-illuminating beam, wherein the improvement comprises:
   said transducer means for generating said scanning beam is a steerable array of ultrasonic transducers located in a helical pattern.

2. An improved ultrasonic intracavitary imaging system in accordance with claim 1 wherein
   an integrated steering circuit is embedded in said probe to which the steerable array of ultrasonic transducers is connected, thus reducing the number of leads required to connect the array of ultrasonic transducers through said probe to said control and processing system.

3. An improved intracavitary ultrasonic imaging system of a type in which a stationary probe supports a mechanically scanning movable ultrasonic transducer, the transducer is connected to a control and processing system, a position coding means is stationary with respect to the probe, and a readout head is moving with the transducer, said readout head reading the position coding means, said readout head connected to the control and processing system where the position signal is decoded, wherein the improvement comprises:
   said position coding means is a sheath coded with a magnetic material, and said readout head is a magnetic head built into said transducer, said readout head transmitting position code through said probe to said control and processing system.

4. An improved intracavitary ultrasonic imaging system of a type in which a stationary probe supports a mechanically scanning movable ultrasonic transducer, the transducer is connected to a control and processing system, a position coding means is stationary with respect to the probe, and a readout head is moving with the transducer, said readout head reading the position coding means, said readout head connected to the control and processing system where the position signal is decoded, wherein the improvement comprises:
   said position coding means is coded with an optically contrasting material, and comprises an optical source and detector built into said probe for reading position code and for transmitting the code through said probe to said control and processing system.

* * * * *